(12) United States Patent
Nguyen et al.

(10) Patent No.: US 9,976,974 B2
(45) Date of Patent: May 22, 2018

(54) OSMOLARITY-RESPONSIVE HYDROGEL SENSORS AND METHOD OF USE

(71) Applicant: University of Utah Research Foundation, Salt Lake City, UT (US)

(72) Inventors: Tram Nguyen, Salt Lake City, UT (US); Jules John Magda, Salt Lake City, UT (US); Seung-Hei Cho, Salt Lake City, UT (US); Prashant Tathireddy, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 109 days.

(21) Appl. No.: 15/006,496

(22) Filed: Jan. 26, 2016

(65) Prior Publication Data

US 2016/0216221 A1   Jul. 28, 2016

Related U.S. Application Data

(60) Provisional application No. 62/125,645, filed on Jan. 27, 2015.

(51) Int. Cl.
*G01N 15/06* (2006.01)
*G01N 27/04* (2006.01)
(Continued)

(52) U.S. Cl.
CPC ............ *G01N 27/045* (2013.01); *G01N 7/00* (2013.01); *G01N 13/04* (2013.01); *G01N 33/48707* (2013.01); *G01N 33/48785* (2013.01); *H01R 4/2404* (2013.01); *H01R 13/533* (2013.01); *H01R 43/16* (2013.01)

(58) Field of Classification Search
CPC .......... G01N 15/0618; G01N 15/0893; G01N 33/18; G01N 27/045; G01N 7/00; G01N 13/04; G01N 33/48707; G01N 33/48785; H01R 4/2404; H01R 13/533; H01R 43/16;
(Continued)

(56) References Cited

U.S. PATENT DOCUMENTS 6,039,940 A * 3/2000 Perrault ................. A61L 15/60
424/443
7,468,397 B2 * 12/2008 Schorzman .......... C08G 77/452
264/1.32
(Continued)

FOREIGN PATENT DOCUMENTS

EP      2404951 A1    1/2012
EP      1644473 B1    1/2014
(Continued)

OTHER PUBLICATIONS

U.S. Appl. No. 62/125,645, filed Jan. 7, 2015, Nguyen (Univ. Utah Res. Found.).
(Continued)

*Primary Examiner* — Manish S Shah
*Assistant Examiner* — Nigel Plumb
(74) *Attorney, Agent, or Firm* — Workman Nydegger

(57) ABSTRACT

Osmolarity-responsive hydrogel sensors, particularly biosensors, containing quaternary ammonium functionality, which are useful for, inter alia, continuous osmolarity monitoring with no pH interference, are disclosed. Methods of using the osmolarity-responsive hydrogels are also disclosed.

22 Claims, 7 Drawing Sheets

(51) Int. Cl.
*G01N 7/00* (2006.01)
*G01N 33/487* (2006.01)
*H01R 4/24* (2018.01)
*H01R 13/533* (2006.01)
*H01R 43/16* (2006.01)
*G01N 13/04* (2006.01)

(58) Field of Classification Search
CPC ............. C08J 2323/00; C08J 2323/10; C08J 2201/02; C08J 2201/06
USPC .................. 73/61.71, 61.41, 53.01, 865.5
See application file for complete search history.

(56) References Cited

U.S. PATENT DOCUMENTS

| | | | | |
|---|---|---|---|---|
| 7,807,473 B2* | 10/2010 | Potyrailo | ............. | G01N 21/78 422/50 |
| 8,131,364 B2* | 3/2012 | Zhu | ............. | A61B 5/14532 607/22 |
| 8,241,574 B2* | 8/2012 | Burles | ............. | A61B 3/125 422/82.05 |
| 8,349,610 B2* | 1/2013 | Stewart | ............. | G01N 33/545 436/108 |
| 8,426,207 B2* | 4/2013 | Stewart | ............. | B01J 39/04 436/108 |
| 8,496,946 B2* | 7/2013 | Coady | ............. | A01N 33/12 424/400 |
| 8,713,997 B2* | 5/2014 | Donsky | ............. | G01N 13/04 73/64.47 |
| 2007/0249059 A1* | 10/2007 | Stewart | ............. | G01N 33/54373 436/148 |

FOREIGN PATENT DOCUMENTS

WO  WO-2009/075561 A2  6/2009
WO  WO-2014/164731 A1  10/2014

OTHER PUBLICATIONS

Kuru, et al., "Preparation of homogeneous polyacrylamide hydrogels by free-radical crosslinking copolymerization", European Polymer Journal 43 (2007) pp. 2913-2921.

* cited by examiner

OSMOLARITY-RESPONSIVE HYDROGEL SENSORS AND METHOD OF USE

CROSS REFERENCE TO RELATED APPLICATIONS

The application claims the benefit of U.S. Application No. 62/125,645 filed Jan. 27, 2015, the entire disclosure of which is incorporated herein by reference.

REFERENCE TO GOVERNMENT GRANTS

This invention was made with government support under IIP1321572 awarded by the National Science Foundation. The government has certain rights in the invention.

FIELD OF THE INVENTION

The invention generally relates to osmolarity-responsive hydrogel. More particularly, the invention relates to osmolarity-responsive hydrogel sensors useful for, inter alia, continuous osmolarity monitoring with substantially no pH interference and methods of their use.

BACKGROUND OF THE INVENTION

Both osmolarity and osmolality are defined in terms of osmoles. An osmole is a unit of measurement that describes the number of moles of a compound that contribute to the osmotic pressure of a chemical solution, i.e., the hydrostatic pressure resulting from a concentration gradient across two sides of a surface, such as across a semi-permeable membrane. Osmolarity is defined as the number of osmoles of solute per volume of solution. It is commonly expressed in terms of osmol/L. For example, a mole of NaCl dissociates fully in water to yield two moles of particles: $Na^+$ ions and $Cl^-$ ions. Each mole of NaCl becomes two osmoles in aqueous solution. Therefore, a 1 mol/L NaCl solution has an osmolarity of 2 osmol/L. Osmolality is defined as the number of osmoles of solute per mass of solvent. It is commonly expressed in terms of osmol/kg.

The measurement of osmolarity is important in many processes (either chemical or biological), such as cell cultivation, fermentation, food and beverage manufacturing, environmental control, water purification, dialysis, bioprocess control, and biological monitoring, but can be complex and difficult. For example, osmolarity is critical in cell cultivation because it has a significant impact on cell growth, viability, density, biologic product concentration, and yield. However, controlling the osmolarity of cell culture media requires instantaneous and constant monitoring under harsh conditions.

Osmolarity of a solution is commonly measured by freezing point depression or boiling point elevation. Unfortunately, these techniques require the extraction of a sample to run the test and cannot be done in situ or in real time. Furthermore, the sample extraction process can contaminate the process, introduce unnecessary risk to the sample purity, and/or reduce the efficacy of the bioprocess. Near-infrared spectroscopy may also be used to measure osmolarity. Another solution in these research/development and industrial applications is the use of sensors to measure the osmolarity without the need to remove a sample from the process vessel. Unfortunately, the current sensors are not as sensitive or accurate as needed, due to pH interference.

Sensors that measure osmolarity are important not only in research/development and industrial applications, but also in biomedical monitoring, clinical medicine, and veterinary science for measuring, for example, the osmolarity of biological fluids, such as serum, blood plasma, saliva, ocular fluid, and urine.

Thus, a need exists for more accurate monitoring of osmolarity in clinical medicine and veterinary science applications and in processes, especially bioprocesses, inter alia, to reduce contamination and improve process yield. The invention is directed to these, as well as other, important ends.

SUMMARY OF THE INVENTION

The invention provides osmolarity-responsive hydrogels useful for, inter alia, continuous osmolarity monitoring with substantially no pH interference.

In one aspect, the invention is directed sensors, particularly biosensors, comprising:

a hydrated, crosslinked copolymer comprising residues of the formula:

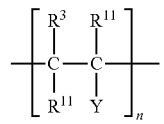

wherein:
n is at least 1,000;
Y is —(C=O)—Z or
Y is

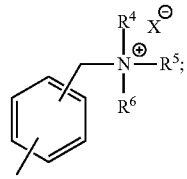

Z is —$NR^1R^2$ or —$OR^7$;

each $R^1$ and $R^2$ is independently H, ($C_1$-$C_6$)alkyl, benzyl, residue derived from —($C_1$-$C_6$)alkylenyl-NH—C=O—CH=$CH_2$, or quaternary ammonium-substituted linker group and counteranion; and optionally, wherein at least a portion of said $R^1$ or said $R^2$ in said copolymer are said residues derived from —($C_1$-$C_6$) alkylenyl-NH—C=O—CH=$CH_2$;

wherein at least a portion of said $R^1$ or said $R^2$ in said copolymer are said quaternary ammonium-substituted linker group;

each $R^3$ is independently H or ($C_1$-$C_6$)alkyl; and
each $R^4$, $R^5$, and $R^6$ is independently ($C_1$-$C_6$)alkyl; and
each $R^7$ is independently ($C_1$-$C_6$)alkyl, benzyl, or quaternary ammonium-substituted linker group and counteranion;

wherein at least a portion of said $R^7$ in said copolymer are said quaternary ammonium-substituted linker group; and wherein said hydrogel is sensitive to changes in osmolarity but substantially insensitive to changes in pH;

each $R^{11}$ is independently H or ($C_1$-$C_4$)alkyl; and a transducer associated with said hydrogel to convert a change in a physical quantity or chemical quantity associated with said hydrogel to an electrical signal.

In yet other aspects, the invention is directed to sensor systems, comprising:

an array of sensors, particularly biosensors, described herein; and a signal transmitter for transmitting to said electrical signal to a controller.

In further aspects, the invention is directed to methods of measuring, including on a continuous basis, osmolarity of a fluid (such as a chemical or biological fluid), comprising:

contacting a hydrogel described herein with said fluid;

measuring a value of a physical change in said hydrogel; and converter said value to an electrical signal;

wherein said physical change is a change in volume, a change in magnetic field, or a change in an optical property.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE INVENTION

Definitions

Figure 1:
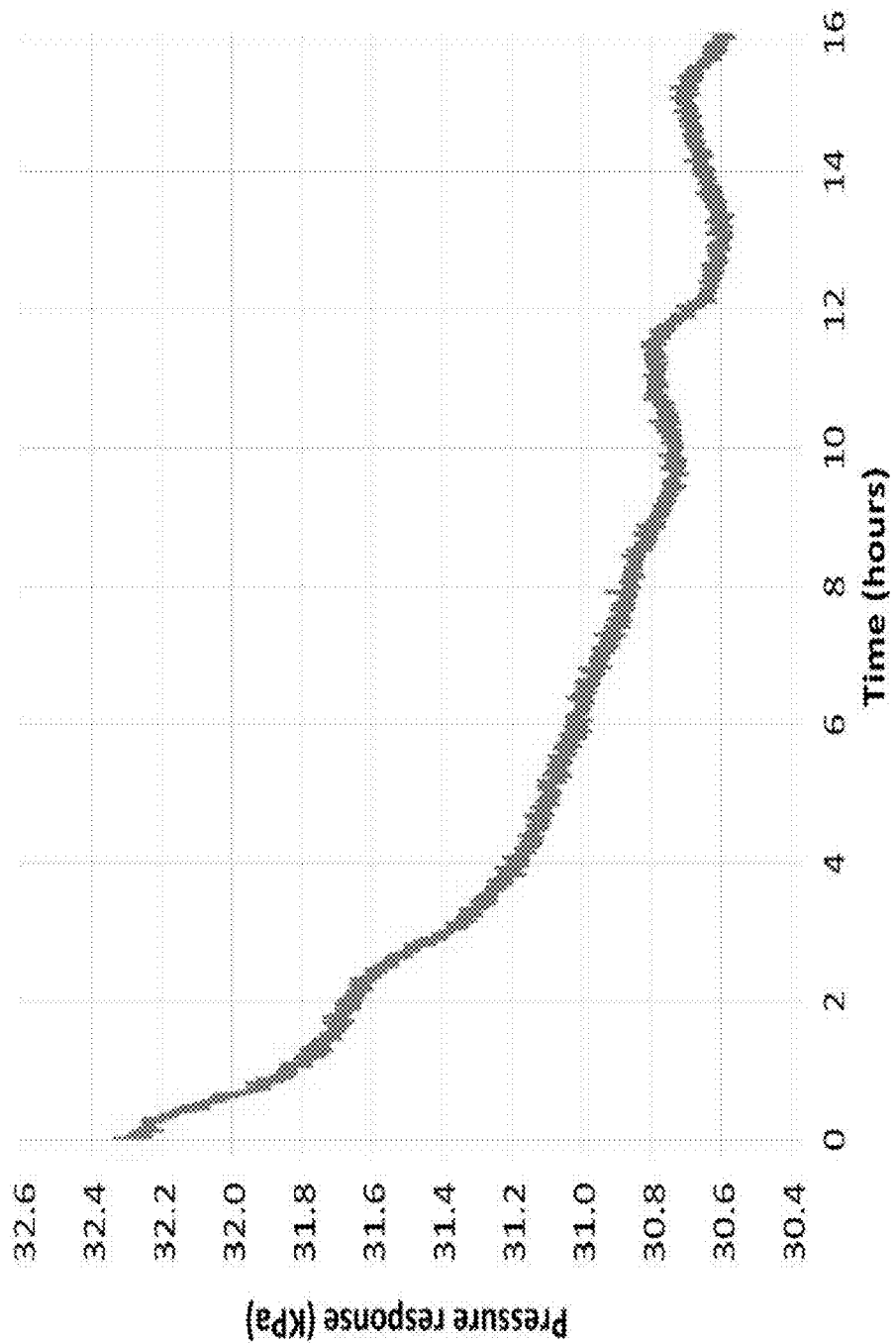
FIG. 1 is a plot of the pressure changes in the chamber over time with a pH change from 7.2 to 7.4 for a hydrogel containing residues of N-[3-(dimethylamino)propyl]acrylamide (DMAPAA), a tertiary amine, at 11 mole %.

The following definitions are provided for the full understanding of terms used in this specification.

As used herein, the article "a" means "at least one," unless the context in which the article is used clearly indicates otherwise.

As used herein, the term "hydrogel" refers to a three dimensional network of polymers that are crosslinked to form water-swellable but water-insoluble structures. The term hydrogel is to be applied to polymers in a dry state (xerogel), as well as in a wet state.

As used herein, the term "osmolarity" refers to the number of osmoles of solute per volume of solution and the term "osmolality" refers to the number of osmoles of solute per mass of solvent. When either term is used herein in reference to the invention, it refers collectively to both osmolarity and osmolality.

As used herein, the term "alkyl" refers to an aliphatic hydrocarbon chain of 1 to about 20 carbon atoms, preferably 1 to 10 carbon atoms, more preferably, 1 to 6 carbon atoms, and even more preferably, 1 to 4 carbon atoms and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 4 carbon atoms.

As used herein, the term "alkylenyl" is a bivalent saturated $(C_1-C_{10})$aliphatic radical (such as ethylene and propylene) regarded as derived from a $(C_2-C_{10})$alkene by opening of the double bond or from a $(C_1-C_{10})$alkane by removal of two hydrogen atoms from different carbon atoms. The ethylene version $(C_2)$ is referred to as "ethylenyl" and the propylene version $(C_3)$ is referred to as "propylenyl" and so on.

As used herein, the term "quaternary ammonium-substituted linker group" refers to a linker group substituted with a quaternary amine group. The linker group may be, for example, a $(C_1-C_6)$alkylenyl group or a $(C_1-C_6)$alkylene oxide group.

As used herein, the term "(meth)acrylamide" refers to both acrylamide and methacrylamide and includes both unsubstituted and substituted versions of the monomers.

As used herein, the term "(meth)acrylic acid" refers to both acrylic acid and methacrylic acid.

As used herein, the term "(meth)acrylate" refers to both acrylate and methacrylate.

As used herein, the term "fluid" refers to chemical fluids and biological fluids (such as growth media and biological fluids from an animal or non-animal). "Biological fluids" of a subject or patient may be selected from the group consisting of saliva, whole blood, plasma, serum, lymph, synovial fluid, peritoneal fluid, pleural fluid, urine, sputum, semen, vaginal lavage, bone marrow, cerebrospinal cord fluid and tears. The biological fluid can be analyzed for osmolarity directly in the body or removed and tested outside of the patient.

As used herein, the term "sensitive," when used in reference to the detecting changes in osmolarity, refers to the ability of a hydrogel to measure osmolarity changes as small as about 5%.

As used herein, the term "substantially insensitive," when used in reference to the detecting changes in pH, refers to the ability of a hydrogel to detect an osmolarity sensor signal change of not more than about 15%, when pH is changed between pH 7.2 and 7.4, when the osmolarity is held substantially constant.

Reference will now be made in detail to the preferred embodiments of the invention, examples of which are illustrated in the drawings and the examples. This invention may, however, be embodied in many different forms and should not be construed as limited to the embodiments set forth herein. In addition and as will be appreciated by one of skill in the art, the invention may be embodied as a product, method, system or process.

Accordingly, in one aspect, the invention is directed to sensors, particularly biosensors, comprising:

a hydrated, crosslinked copolymer comprising residues of the formula:

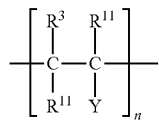

wherein:
n is at least 1,000;
Y is —(C=O)—Z or
Y is

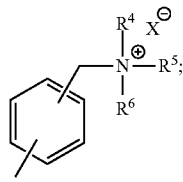

Z is –NR$^1$R$^2$ or —OR$^7$;
each R$^1$ and R$^2$ is independently H, (C$_1$-C$_6$)alkyl, benzyl, residue derived from —(C$_1$-C$_6$)alkylenyl-NH—C=O—CH=CH$_2$, or quaternary ammonium-substituted linker group and counteranion; and optionally, wherein at least a portion of said R$^1$ or said R$^2$ in said copolymer are said residues derived from —(C$_1$-C$_6$)alkylenyl-NH—C=O—CH=CH$_2$;

wherein at least a portion of said R$^1$ or said R$^2$ in said copolymer are said quaternary ammonium-substituted linker group;

each R$^3$ is independently H or (C$_1$-C$_6$)alkyl; and
each R$^4$, R$^5$, and R$^6$ is independently (C$_1$-C$_6$)alkyl; and
each R$^7$ is independently (C$_1$-C$_6$)alkyl, benzyl, or quaternary ammonium-substituted linker group and counteranion;

wherein at least a portion of said R$^7$ in said copolymer are said quaternary ammonium-substituted linker group; and wherein said hydrogel is sensitive to changes in osmolarity but substantially insensitive to changes in pH;

each R$^{11}$ is independently H or (C$_1$-C$_4$)alkyl; and
wherein said hydrogel is sensitive to changes in osmolarity but substantially insensitive to changes in pH; and a transducer associated with said hydrogel to convert a change in a physical quantity or chemical quantity associated with said hydrogel to an electrical signal.

The inventors have discovered that osmotically-responsive, but pH insensitive hydrogels can be prepared by selective incorporation of a quaternary ammonium functional group. This has been achieved and has significant utility in making a wide range of hydrogel-based sensors useful, for example, in determinations of osmolarity in many chemical and biological processes, such as cell cultivation, fermentation, food and beverage manufacturing, environmental control, water purification, dialysis, bioprocess control, biological monitoring, biomedical monitoring, clinical medicine, and veterinary science.

The hydrogels useful in the sensors of the invention may contain the reaction product of the monomer containing the quaternary ammonium-functionalized (meth)acrylamide or quaternary ammonium-functionalized vinylbenzyl with at least one second monomer, which is preferably crosslinked with a bifunctional monomer. Preferably, the second monomer is selected from substituted or unsubstituted (meth)acrylamide (such as acrylamide, methacrylamide, N,N-dimethylacrylamide, and N-isopropylacrylamide), more preferably unsubstituted acrylamide. Other second monomers may be included, provided that they do not substantially interfere with the measurement of osmolarity and do not substantially increase the sensitivity of the hydrogel to pH. Other suitable second monomers include, but are not limited to, (meth)acrylic acid, hydroxy(C$_1$-C$_6$)alkylacrylates (such as hydroxethyl acrylate), hydroxy(C$_1$-C$_6$)alkylmethacrylates (such as hydroxyethyl methacrylate), alkylethers (such as ethylene oxide and propylene oxide), vinyl ethers, N-vinyl pyrrolidone (including those comprising an anionic moiety selected from the group consisting of carboxylate, sulfate, sulfonate, and phosphate), styrene copolymerized with allyl alcohol, 4-vinylphenol, vinyl acetate monomers, ethylene copolymerized with vinyl acetate, zwitterionic monomers (such as zwitterionic sulfobetaine monomers), and fully-neutralized sodium acrylate monomers. Since the incorporation of carboxylic acid groups into hydrogels can increase their sensitivity to pH and salt concentration, it is preferred not to include or minimize monomers with carboxylic acid groups into the hydrogels, as the sensors seek to minimize or eliminate pH interference.

The hydrogels useful in the sensors of the invention may be prepared by synthetic methods known in the art, including via free-radical crosslinking copolymerization of, for example, acrylamide-based monomers with a divinyl monomer (crosslinker) in aqueous solution, via radiation-induced free radical polymerization reaction, or ultrasonic free radical polymerization reaction. The hydrogels may be prepared via free-radical crosslinking copolymerization using UV irradiation to generate free radicals, or by using thermal methods to generate free radicals from peroxides or persulfate thermal free radical initiators. The hydrogels may also be prepared using controlled radical polymerization techniques, such as reversible addition-fragmentation chain-transfer polymerization (RAFT). The hydrogels may also be prepared using a suitable catalyst, such as a Ziegler-Natta catalyst or a metallocene catalyst. The hydrogels may also be prepared using living polymerization techniques, such as living anionic polymerization, living cationic polymerization, living ring-opening metathesis polymerization, or living free radical polymerization.

In certain embodiments, said —(C$_1$-C$_4$)alkylenyl-NH—C=O—CH=CH$_2$ is -methylenyl-NH—C=O—CH=CH$_2$.

In certain embodiments, said quaternary ammonium-substituted (C$_1$-C$_6$)alkyl can be represented by the formula:

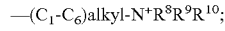

—(C$_1$-C$_6$)alkyl-N$^+$R$^8$R$^9$R$^{10}$;

wherein each R$^8$, R$^9$, and R$^{10}$ is independently (C$_1$-C$_{10}$)alkyl, (C$_2$-C$_{10}$)alkenyl, (C$_1$-C$_{10}$)alkynyl, phenyl, napthyl, or benzyl, wherein each of the foregoing moieties may be unsubstituted or substituted with, for example, amide, ester, ether, urethane, or urea. In certain embodiments, said quaternary ammonium-substituted $(C_1-C_6)$alkyl is tri$(C_1-C_6)$ alkyl ammonium $C_3$ alkyl, especially trimethyl ammonium n-propyl.

In certain embodiments, Y is —$C_6H_4CH_2N^+(CH_3)_3Cl^-$.

In certain embodiments, said copolymer is formed from the reaction of wherein said copolymer is formed from the reaction of acrylamide, quaternary ammonium-functionalized monomer, and N,N-methylene-bisacrylamide. In certain embodiments, said quaternary ammonium-functionalized monomer is, for example, 3-acrylaminopropyl) trimethylammonium chloride, quaternary ammonium (meth)acrylate, or (ar-vinylbenzyl)trimethyl ammonium chloride.

In certain embodiments, said copolymer comprises the reaction product of:
  about 75 mole % to about 95 mole % of acrylamide;
  about 6 mole % to about 15 mole % of 3-acrylaminopropyl)trimethylammonium chloride or (ar-vinylbenzyl)trimethyl ammonium chloride; and
  about 0.5 mole % to about 10 mole % of N,N-methylene-bisacrylamide.

In certain embodiments, said copolymer comprises the reaction product of:
  about 78 mole % to about 92 mole % of acrylamide;
  about 7 mole % to about 12 mole % of 3-acrylaminopropyl)trimethylammonium chloride or (ar-vinylbenzyl)trimethyl ammonium chloride; and
  about 1 mole % to about 5 mole % of N,N-methylene-bisacrylamide.

In certain embodiments, said copolymer comprises the reaction product of:
  about 87 mole % to about 89 mole % of acrylamide;
  about 9 mole % to about 11 mole % of 3-acrylaminopropyl)trimethylammonium chloride or (ar-vinylbenzyl)trimethyl ammonium chloride; and
  about 2 mole % to about 4 mole % of N,N-methylene-bisacrylamide.

In certain embodiments, said counteranion is an anion selected from the group consisting of halide (such as fluoride ion, chloride ion, or iodide ion) and methyl sulfate. Chloride ion is preferred.

The hydrogel useful in the sensors of the invention may be crosslinked in a number of ways, as described for example in U.S. Patent Publication No. 20070249059, expressly incorporated by reference herein. Alternatively, hydrogels may be crosslinked with ionic species or by incorporation of self-associating monomers resulting in physical crosslinking or may be effectively be rendered insoluble by incorporation into an interpenetrating network.

The hydrogel polymers useful in the sensors of the invention may be cured or crosslinked by techniques known in the art, such as for example, thermal free radical curing, ultraviolet (UV) curing, reversible addition-fragmentation chain-transfer polymerization (RAFT) curing, and living polymerization curing techniques.

In certain embodiments, the cationic quaternary amine polymer hydrogels may be formed by in situ free radical polymerization of a water-soluble monomer (such as those described herein) in the presence of water, preferably by ultra-violet curing with initiator(s) and multi-functional cross-linking agent(s). For example, an appropriate monomer, water, optional additional polymerization enhancer (e.g. salt, for example, sodium chloride, potassium chloride, etc.), initiator or catalyst (e.g. α-hydroxy-1,α-dimethylacetophenone in DMSO, etc.), and a multi-functional cross-linker (e.g. methylene-bis-acrylamide, etc.) are combined, placed in a mold, and exposed to ultraviolet radiation as is known in the art.

As mentioned above, the present hydrogels may include a buffer system to help control the pH, help prevent discoloration, and/or help prevent breakdown due to the extended presence of water (i.e. help prevent hydrolysis). Buffers, if any, are preferably added to the mixture prior to curing. Suitable buffers include, for example, but are not limited to, sodium potassium tartarate, and/or sodium phosphate monobasic, both of which are commercially readily available from, for example, Aldrich Chemical Co., IN. The use of a buffer system with the present hydrogel is preferred to provide the hydrogel with a commercially suitable shelf-life (i.e. a shelf-life of over one year) without discoloration.

As is also mentioned above, other additives may be included in the present hydrogels either before or after curing (i.e. pharmaceuticals such as antibiotics, disinfectants and the like, humectants, plasticizers, etc.). The appropriateness of such additives is generally dependent upon the intended end use of the particular hydrogel sensor.

As is mentioned above, initiators are preferably used in the polymerization of the present hydrogels. Examples of initiators which may be used include, for example, IRGACURE® 184 (1-hydroxycyclohexyl phenyl ketone), and DAROCURE® 1173 (α-hydroxy-1,αdimethylacetophenone) which are both commercially available from Ciba-Geigy Corp. These UV catalysts are preferred because they are non-yellowing. Other initiators which maintain the preferred water-white and water-clear appearance of the hydrogels are preferred. However, additional examples of initiators (which may be photo initiators or thermal initiators) may include benzoyl peroxide, azo-bis-isobutyro-nitrile, di-t-butyl peroxide, bromyl peroxide, cumyl peroxide, lauroyl peroxide, isopropyl percarbonate, methylethyl ketone peroxide, cyclohexane peroxide, t-butylhydroperoxide, di-t-amyl peroxide, dicumyl peroxide, t-butyl perbenzoate, benzoin alkyl ethers (such as benzoin, benzoin isopropyl ether, and benzoin isobutyl ether), benzophenones (such as benzophenone and methyl-o-benzoyl benzoate), acetophenones (such as acetophenone, trichloroacetophenone, 2,2-diethoxyacetophenone, p-t-butyltrichloro-acetophenone, 2,2-dimethoxy-2-phenyl-acetophenone, and p-dimethylaminoacetophenone), thioxanthones (such as xanthone, thioxanthone, 2-chlorothioxanthone, and 2-isopropyl thioxanthone), benzyl 2-ethyl anthraquinone, methylbenzoyl formate, 2-hydroxy-2-methyl-1-phenyl propane-1-one, 2-hydroxy-4'-isopropyl-2-methyl propiophenone, e-hydroxy ketone, tetramethyl thiuram monosulfide, allyl diazonium salt, and combination of camphorquinone and ethyl 4-(N,N-dimethylamino)benzoate. Other initiators may be found in, for example, Berner, et al., "Photo Initiators—An Overview," J. Radiation Curing (April 1979), pp. 2-9.

The amount of initiator is preferably within the range of about 0.02 to 2.0% by weight based on total amount of monomer, and more preferably within the range of about 0.05 to 0.5% by weight based on total amount of monomer.

UV curing parameters to achieve desired polymer properties are well known to those skilled in the art. An initiator for the present purposes tends to operate by absorbing select wavelengths of UV light, and breaking down into free radicals to initiate polymerization. The wavelengths and curing area set the style of UV bulb used in the curing process. Inhibition of polymerization due to dissolved oxygen, monomer preservatives, or other components may be overcome by changing the power, by pulsing, and/or by using catalyst accelerators. The amount of residual monomer (after polymerization) is preferred to be less than about 3% for good biocompatability.

Crosslinking agents are preferably used to crosslink the hydrogels useful in the sensors of the invention. Examples of multi-functional crosslinking agents that may be used are methylene-bis-acrylamide (BIS) and diethylene glycol diacrylate, which are both commercially available from Polysciences, Inc., Warrington, Pa. Additional examples of crosslinking agents that may be acceptable for use in the present invention include ethylene glycol diacrylate, triethylene glycol-bis-methacrylate, ethylene glycol-bis-methacrylate, ethylene glycol-dimethacrylate, bis-acrylamide, triethyleneglycol-bis-acrylate, 3,3'-ethylidene-bis(N-vinyl-2-pyrrolidone), trimethylolpropate trimethacrylate, glycerol trimethacrylate, polyethylene glycol dimethacrylate, and other polyacrylate and polymethacrylate esters.

The amount of crosslinking agent used is preferably within the range of about 0.02% by weight to about 5.0% by weight based on total amount of monomer, and more preferably within the range of about 0.05% by weight to 2.0% by weight, based on total amount of monomer.

In certain embodiments, the sensors further comprise magnetic particles associated with said hydrogel.

In certain embodiments, wherein said hydrogel is contained in a chamber of a fixed volume.

In certain embodiments, said transducer measures change in volume (volumetric), magnetic field, optical density, refractive index, optical transmittance, fluorescence, ionic mobility, resistance, AC conductivity, capacitance, or viscoelastic property, such as for example, using the appropriate pressure transducer, a magnetic sensor, an optical sensor, an electrical sensor, or a viscoelastic sensor.

In certain embodiments, said sensor is a single-use sensor.

In certain embodiments, the sensors further comprise a signal transmitter for transmitting to said electrical signal to a controller. In certain embodiments, said signal transmitter is reusable. In certain embodiments, said signal transmitter is wireless.

In another aspect, the invention is directed to sensor systems, comprising:

an array of sensors, particularly biosensors, described herein; and a signal transmitter for transmitting to said electrical signal to a controller. In certain embodiments, said array is prepared by inkjet printing.

In further aspects, the invention is directed to methods of measuring, including on a continuous basis, osmolarity of a fluid, especially a biological fluid or a fluid in a chemical process, comprising:

contacting a hydrogel described herein with said fluid; and measuring a value of a physical change in said hydrogel; and converter said value to an electrical signal;

wherein said physical change is a change in volume, a change in magnetic field, or a change in an optical property.

The hydrogels useful in the sensors of the invention are sterilizable using standard sterilization techniques, including but not limited to gamma irradiation, autoclave, and ethylene oxide, and the like.

The hydrogels useful in the sensors of the invention may be used as reference sensors for other smart hydrogels, which respond to other chemical and physical stimuli and also respond to osmolarity changes but for which pH is an interferent. As used herein, the term "smart" refers to a hydrogel's ability to selectively bind one or more particular analyte species at the selective exclusion of one or more other species.

The hydrogels useful in the sensors of the invention provide a reversible response to osmolarity changes but substantially no response to pH changes, the most common interferent in sensors used in research/development and industrial processes. Furthermore, the hydrogels provide real-time measurement of osmolarity changes and may be used in situ and/or for continuous osmolarity monitoring.

The sensors of the invention may be constructed into a sensor system, including for example, a substrate having a least one hydrogel sensor associated therewith; a magnetometer adjacent to the at least one hydrogel sensor; and a plurality of magnetic particles associated with the at least one hydrogel sensor, as described in WO 2014/164,731 (U.S. National Stage Entry application Ser. No. 14/774,070, herein incorporated by reference in its entirety.

The hydrogel sensors of the invention take advantage of a change in measurable properties of hydrogels upon a change in osmolarity of the process or biochemical fluid. Generally, the osmolarity change provokes a change in a measurable property of the hydrogel, and information regarding the osmolarity may be extracted by measuring the change in the measurable property. Accordingly, the hydrogel-based sensor systems may include suitable mechanisms to detect the change in the osmolarity.

In certain embodiments, the hydrogel may respond to the change in osmolarity with a change in physical properties, electrical properties, optical properties, mechanical properties, chemical properties or a combination thereof. In certain embodiments, the hydrogel may respond to the change in osmolarity with a change in size/volume, density, porosity, index of refraction, elasticity, viscosity, modulus or a combination thereof. In certain embodiments, the hydrogel may respond to the change is osmolarity by swelling or shrinking relative to its initial volume.

In certain embodiments, the hydrogel may respond to the change in osmolarity by swelling to occupy at least about 1.001 times its initial volume, at least about 1.01, at least about 1.1, at least about 1.2, at least about 1.3, at least about 1.4, at least about 1.5, at least about 1.6, at least about 1.7, at least about 1.8, at least about 1.9, at least about 2.0, at least about 2.5, at least about 3.0, at least about 3.5, at least about 4.0, at least about 4.5, at least about 5.0, at least about 6.0, at least about 7.0, at least about 8.0, at least about 9.0, at least about 10.0, at least about 11.0, at least about 12.0, at least about 13.0, at least about 14.0, at least about 15.0, at least about 20.0, or at least about 25.0 times its initial volume. In certain embodiments, the hydrogel may response to the change in osmolarity by swelling to occupy at most about 100 times its initial volume, at most about 90, at most about 80, at most about 75, at most about 70, at most about 65, at most about 60, at most about 55, at most about 50.0, at most about 45.0, at most about 40.0, at most about 35.0, at most about 30.0, at most about 29.0, at most about 28.0, at most about 27.0, at most about 26.0, at most about 25.0, at most about 24.0, at most about 23.0, at most about 22.0, at most about 21.0, at most about 20.0, at most about 19.0, at most about 18.0, at most about 17.0, at most about 16.0, at most about 15.0, at most about 14.0, at most about 13.0, at most about 12.0, at most about 11.0, at most about 10.0, at most about 9.0, at most about 8.0, at most about 7.0, at most about 6.0, or at most about 5.0 times it initial volume. This includes embodiments where the hydrogel responds to the change in osmolarity by swelling to occupy volumes ranging from about 1.001 to about 100 times its initial volume, including, but not limited to, volumes ranging from about 1.01 to about 50 times its initial volume, or volumes ranging from about 1.1 to about 25.0 times its initial volume.

Alternatively, in another embodiment, in response to an osmolarity change in the fluid sample, the hydrogel undergoes a volumetric contraction resulting in a downward displacement of the deflectable arm of the microcantilever. Devices for evaluating a chemical or physical property of a fluid are described for example in U.S. Patent Publication No. 2007/0249059, expressly incorporated by reference herein.

In one embodiment, the hydrogel is disposed on one side of a microcantilever. In another embodiment the microcantilever is formed on a substrate separate from the surface including the sensing material. Conventional semiconductor processing technology may be used to form the microcantilever. Various configurations and orientations of the microcantilever may be used. The microcantilever includes an overhang portion which extends over the edge of the microcantilever substrate and allows for the substrate and the surface containing the sensing material to be positioned in close proximity to one another such that the deflectable arm of the microcantilever is situated above and in contact with the sensing material. A micromanipulator may be used to position and align the components. The deflectable arm of the microcantilever includes at least one measurable physical property which changes when the deflectable arm deflects in response to a volumetric change of the hydrogel sensor. The devices described herein also provide a detecting means in the form of various electric circuits which detect a change in position of the deflectable arm.

The microcantilever may be calibrated to correlate a measured change in volume of hydrogel with the osmolarity of the fluid. In the case where a osmolarity change is not detectable, the microcantilever will not deflect and therefore the measurements taken before and after the introduction of the fluid sample will be substantially the same.

One exemplary sensor is a micro-electro-mechanical systems (MEMS) device comprising a piezoresistive microcantilever 20 µM wide, 300 µM long and 3 µM thick and surrounding die, and wire-bonded connector and female pin block. Nominal resistance across the cantilever is 2.2 kOhms and increases approximately 1 Ohm for each micron the cantilever tip is deflected from neutral. In this embodiment, a hydrogel is secured to a rigid substrate and positioned against the microcantilever such that swelling of the hydrogel deflects the micro-cantilever.

The device may further comprise a signaling component that undergoes a change such as a change in resistance, resonant frequency, electrical output, or capacitance in response to very small movements of the microcantilever arm, or in the case of a resonator, to the rheological properties of the materials with which it is contact.

On example of the basic construction of a fully functional sensor involves determining the neutral resistance of the sensor, then affixing a substrate and hydrogel to the die such that the hydrogel deflects the cantilever as it swelled. In this exemplary approach, hydrogel polymers may be drawn and cured as fibers with approximately 25 µM diameter, cut to approximately 200 µM long sections, and cured on a silane-treated silicon wafer fragment. This fragment is then affixed against the sensor die with epoxy to create a "hydrogel fiber sensor."

Alternatively, the surface of silane treated silicon wafers may be coated with a hydrogel polymer solution in an even continuous layer; achieved by way of natural surface tension of poured polymer, spin coating, or surface repulsion from the low-surface-energy side of Mylar film placed on top of the wet hydrogel polymer. Hydrogel sensors can also readily be prepared using photolithographic methods.

It will be apparent to those skilled in the art that various modifications and variations can be made in the present invention and specific examples provided herein without departing from the spirit or scope of the invention. Thus, it is intended that the present invention cover the modifications and variations of this invention that come within the scope of any claims and their equivalents.

EXAMPLES

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

Example 1: Preparation of Hydrogels

Materials:
Acrylamide (AAM)
N-[3-(dimethylamino)propyl]acrylamide (DMAPAA)
N,N-methylenebisacrylamide (BIS)
(3-acrylamidopropyl)trimethylammonium chloride (ATMA),
(Vinylbenzyl)trimethylammonium (VTMA)
4-(2-hydroxyethyl)piperazine-1-ethanesulfonic acid (HEPES)
Ammonium peroxydisulfate (APS)
N,N,N',N'-tetramethylenediamine (TEMED)
Phosphate buffer saline pH=7.4 (1×PBS) Cell culture media—CDM4CHO, Dynamis Hydrogels were synthesized by radical polymerization using thermal initiator at ambient room conditions. The basic components of the hydrogel include AAM as the backbone, ATMA, VTMA, or DMAPAA as the functional monomer, and BIS as the cross-linker. Stock solutions, including 30 weight % AAM and 2 weight % BIS, were prepared ahead of time in 0.1 M HEPES. Thermal initiator stock solution were prepared by dissolving APS in HEPES to make a 20 mg/mL solution. Pre-gel solutions were made by adding functional monomer, AAM, and BIS in a 1.5 mL centrifuge tube. Molar percent of monomers were calculated with certain ratio and diluted with additional HEPES to make 13 weight % (monomer/solvent) solution. Initiator APS was calculated so that 0.2 mole % of total moles of monomers and the amount of TEMED is ⅒ of APS. Pre-gel solutions were mixed well using vortex mixer. After that, pre-gel solutions were purged with argon gas for 10 minutes. Then, the thermal initiators (TEMED and APS) were be added. Pre-gel solutions were quickly injected into a mold made by two hydrophobized glass slides with a 400 µm Teflon spacer in between and cured for 12 hours at room temperature. After polymerization, the gels were removed from the mold and washed with deionized water to remove excess monomers. Consequently, hydrogels were conditioned in three cycles of deionized water and 1×PBS and finally stored in 1×PBS at ambient conditions until being used.

The following hydrogel compositions were prepared:

| Hydrogel | Composition (molar ratio) |
| --- | --- |
| 1 (invention) | AAm:ATMA:BIS (89:9:2) |
| 2 (invention) | AAm:ATMA:BIS (87:11:2) |
| 3 (comparative: tertiary amine) | AAm:DMAPAA:BIS (87:11:2) |
| 4 (invention) | AAm:ATMA:BIS (78:20:2) |

-continued

| Hydrogel | Composition (molar ratio) |
|---|---|
| 5 (invention) | AAm:ATMA:BIS (93:5:2) |
| 6 (invention) | AAm:VTMA:BIS (87:11:2) |

Example 2: Osmolarity-Response Hydrogel (1×PBS)

The hydrogels prepared in Example 1 were each loaded in a confined chamber. Because the chamber volume is constant, volume changes of the hydrogels cause pressure changes. The osmolarity of the test fluid was adjusted using 1× phosphate-buffered saline. A change in osmolarity was monitored by measuring conductivity of the solution (as representative for osmolarity).

Figure 2:
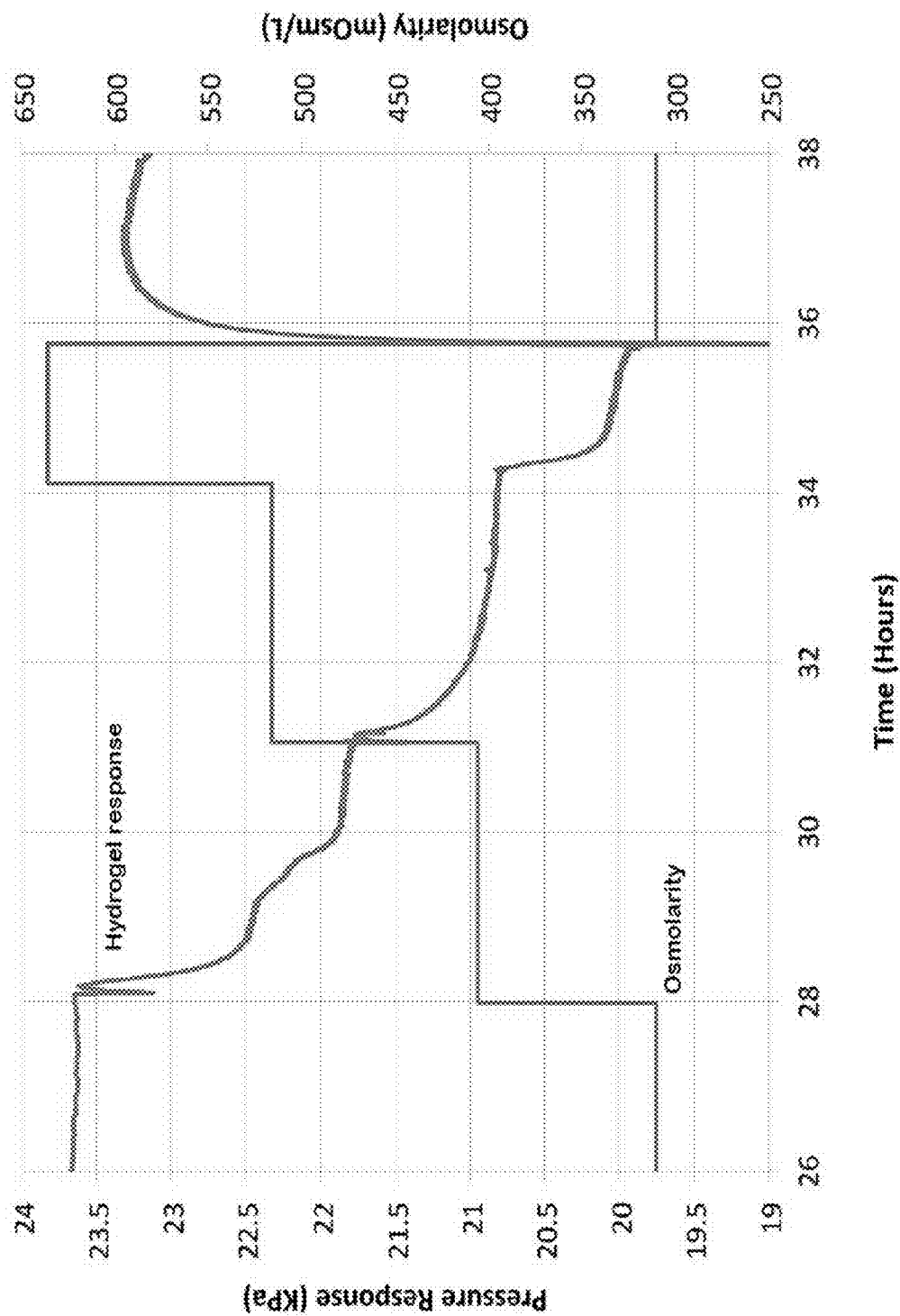
FIG. 2 is a plot of the pressure changes in the chamber over time as the concentration of the 1× phosphate-buffered saline (osmolarity) was increased stepwise for an exemplary hydrogel (hydrogel containing residues of (3-acrylamidopropyl)trimethylammonium chloride (ATMA), a quaternary amine, at 11 mole %) used in the sensors of the invention.
Figure 7:
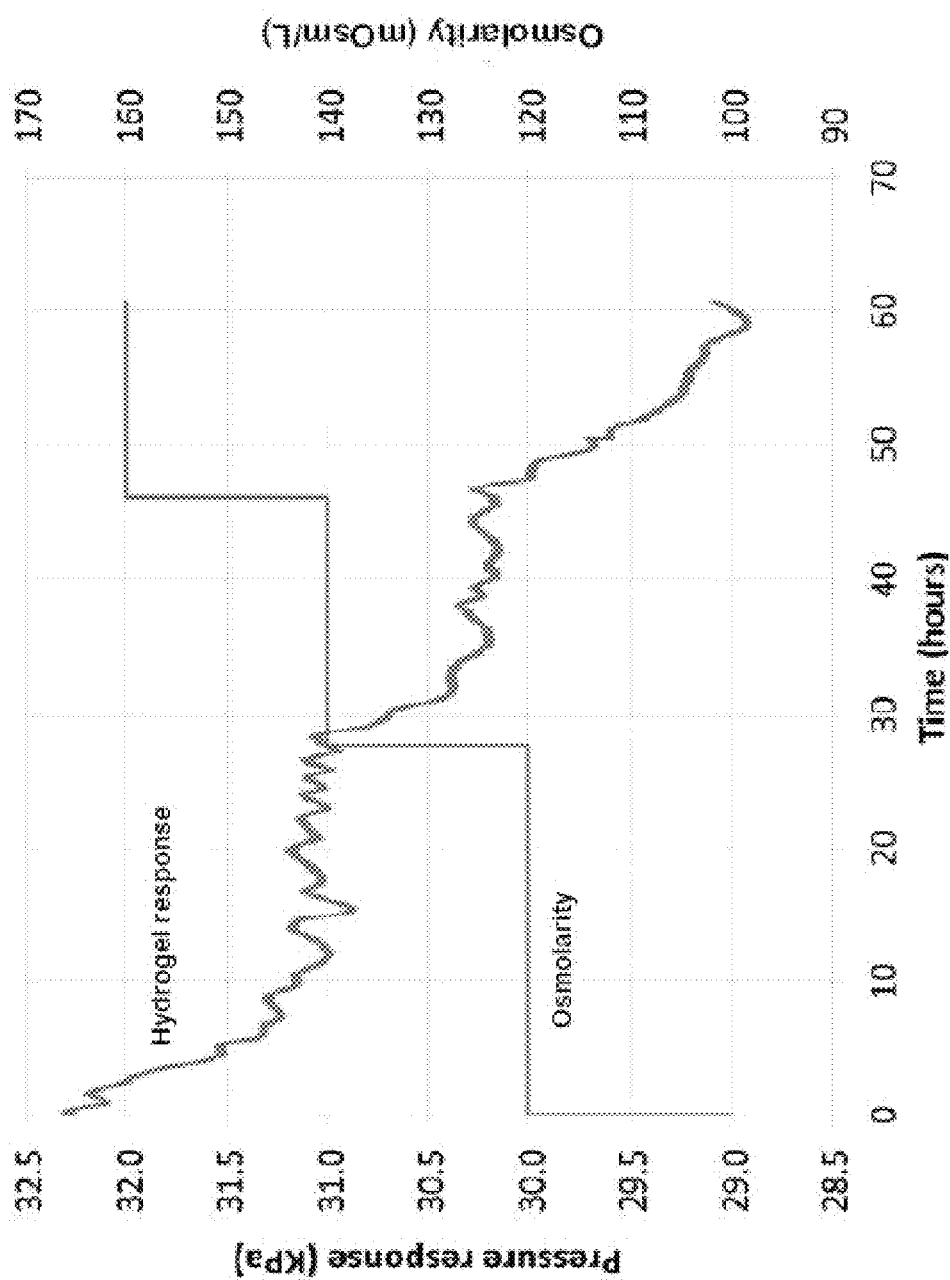
FIG. 7 is a plot of the pressure changes in the chamber over time with a pH change from 7.2 to 7.4 for an exemplary (hydrogel containing residues of (vinylbenzyl)trimethylammonium (VTMA), a quaternary amine, at 9 mole %) used in the sensors of the invention.

The pressure changes in the chamber were monitored over time as the concentration of the 1× phosphate-buffered saline was increased stepwise. FIG. 2 shows the response for Hydrogel 2. FIG. 7 shows the response for Hydrogel 6 over a 60-hour period. As can be seen, Hydrogel 2 shrinks (pressure decreases), as osmolarity (measured via conductivity) increases and then reversibly swells (pressure increases) when osmolarity decreases over a 12-hour period.

Example 3: Osmolarity-Response Hydrogel (Cell Culture Media CDM4CHO)

The hydrogels prepared in Example 1 were each loaded in a confined chamber. Because the chamber volume is constant, volume changes of the hydrogels cause pressure changes. The osmolarity of the test fluid was adjusted using cell culture media (CDM4CHO). A change in osmolarity was monitored by measuring conductivity of the solution (as representative for osmolarity).

Figure 3:
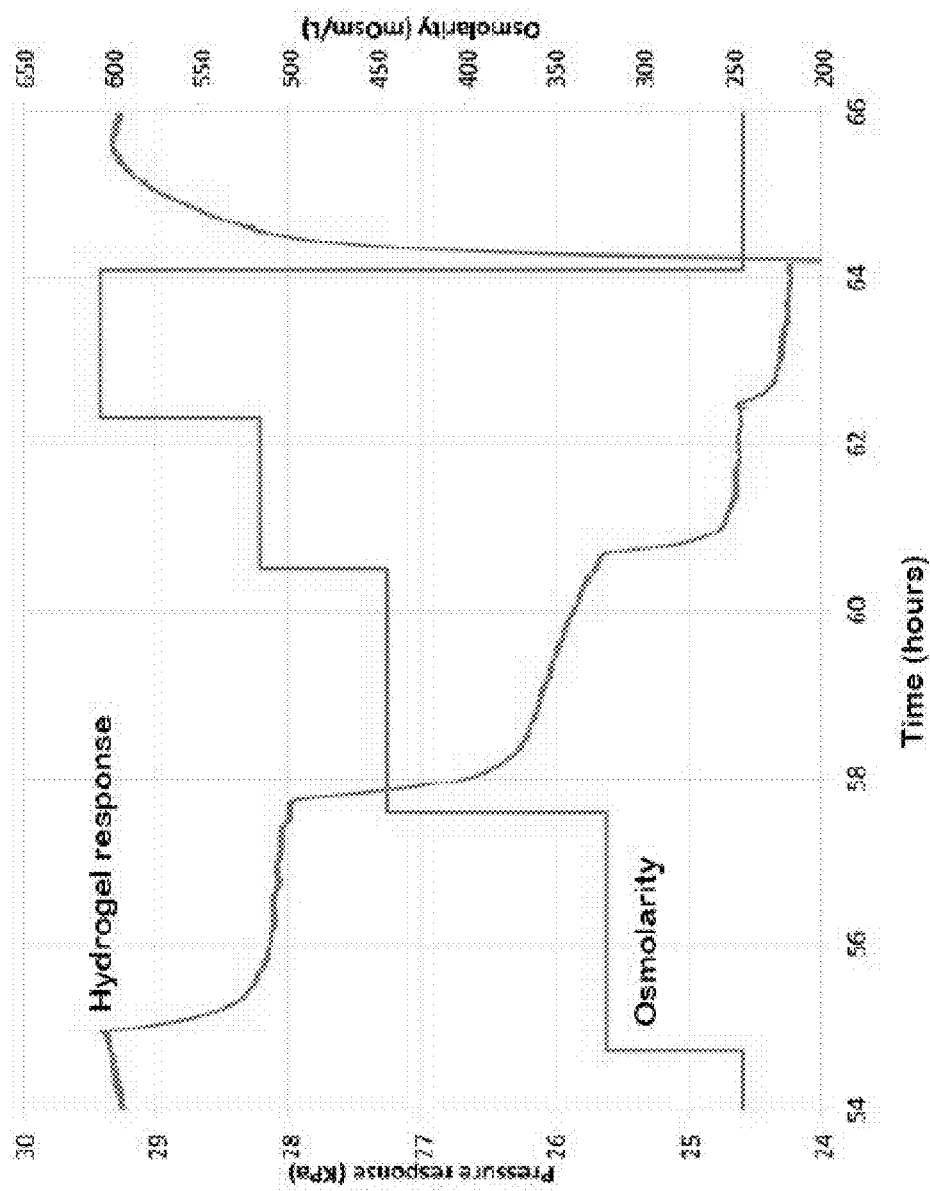
FIG. 3 is a plot of the pressure changes in the chamber over time as the concentration of the cell culture media (CDM4CHO; Dynamis) (osmolarity) was increased stepwise for an exemplary (hydrogel containing residues of (3-acrylamidopropyl)trimethylammonium chloride (ATMA), a quaternary amine, at 11 mole %) used in the sensors of the invention.

The pressure changes in the chamber were monitored over time as the concentration of the cell culture media (CDM4CHO) was increased stepwise. FIG. 3 shows the response for Hydrogel 2. As can be seen, Hydrogel 2 shrinks (pressure decreases), as osmolarity (measured via conductivity) increases over 10 seconds.

Example 4: Osmolarity-Response Hydrogel (as a Function of pH)

Figure 4:
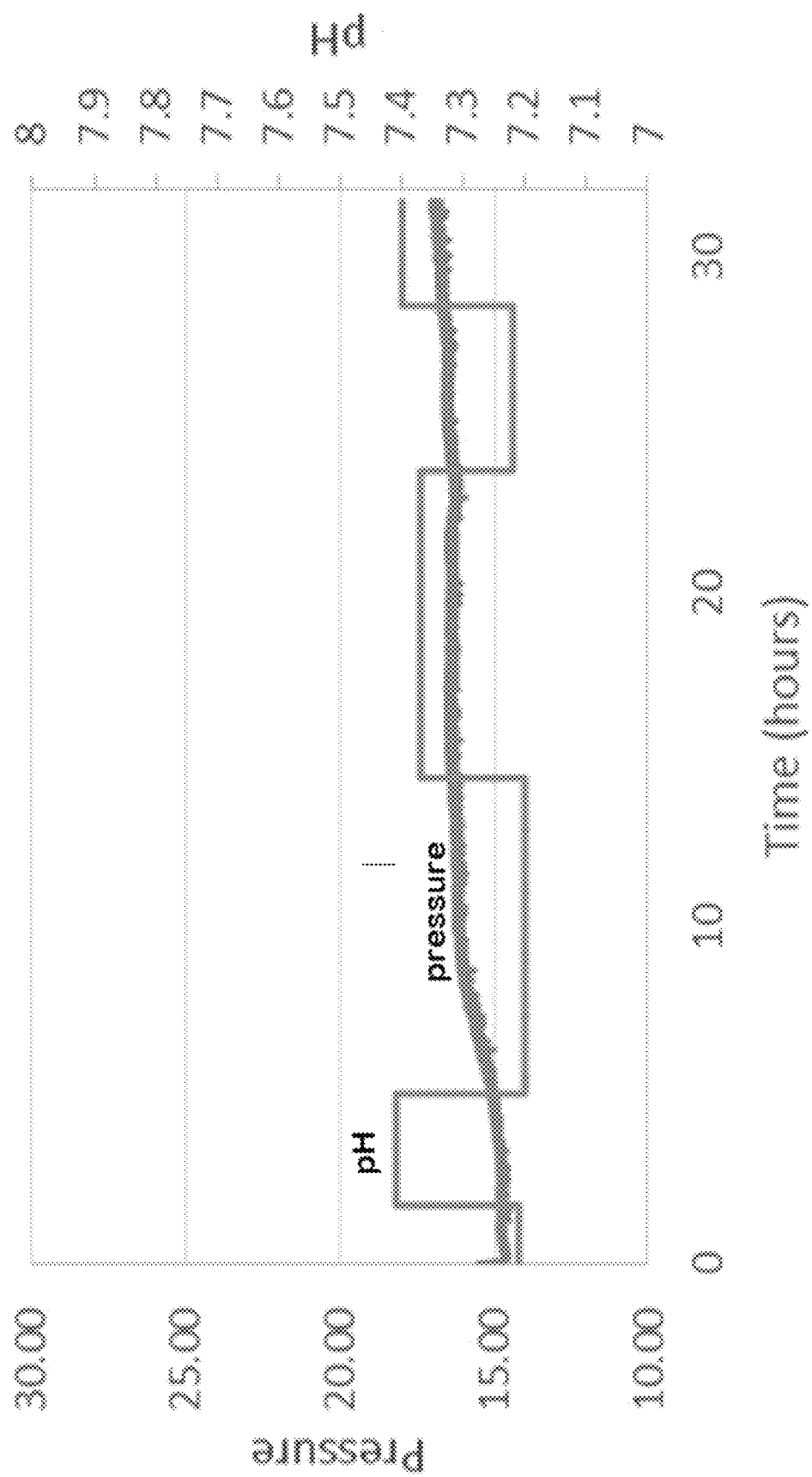
FIG. 4 is a plot of the pressure changes in the chamber over time with a pH change from 7.2 to 7.4 for an exemplary (hydrogel containing residues of (3-acrylamidopropyl)trimethylammonium chloride (ATMA), a quaternary amine, at 11 mole %) used in the sensors of the invention.

The hydrogels prepared in Example 1 were each loaded in a confined chamber. Because the chamber volume is constant, volume changes of the hydrogels cause pressure changes. The pH of the test fluid was adjusted. The pressure changes in the chamber were monitored over time (30 hours) as the pH of the media surrounding the hydrogel was stepwise changed between pH 7.2 and pH 7.4. FIG. 4 shows the response for Hydrogel 2. As can be seen, the pressure of the Hydrogel 2 does not substantially change over the 30 hour period. FIG. 1 shows the response for Hydrogel 3 (comparative). As can be seen, the comparative hydrogel containing the tertiary amine had significant pH interference, thus cannot be applied for sensing osmolarity in cell culture media.

Example 5: Mechanical Properties of Osmolarity-Response Hydrogel

The mechanical properties of the osmolarity-responsive hydrogels of Example 1 were tested. Molar percent of crosslinker BIS was kept at 2%. Molar percent of quaternary amine (ATMA) was varied in the range from 5 to 20. The properties are summarized in Table 1.

TABLE 1

| Hydrogel | Composition | Mechanical Hardness | Response with Osmolarity |
|---|---|---|---|
| 1 (invention) | AAm:ATMA:BIS (89:9:2) | Good mechanical strength | Good response |
| 2 (invention) | AAm:ATMA:BIS (87:11:2) | Soft, easy broken | Good response |
| 4 (invention) | AAm:ATMA:BIS (78:20:2) | Does not have fixed shape | Cannot be used in pressure sensor |
| 5 (invention) | AAm:ATMA:BIS (93:5:2) | Good mechanical strength | No response |

Figure 5:
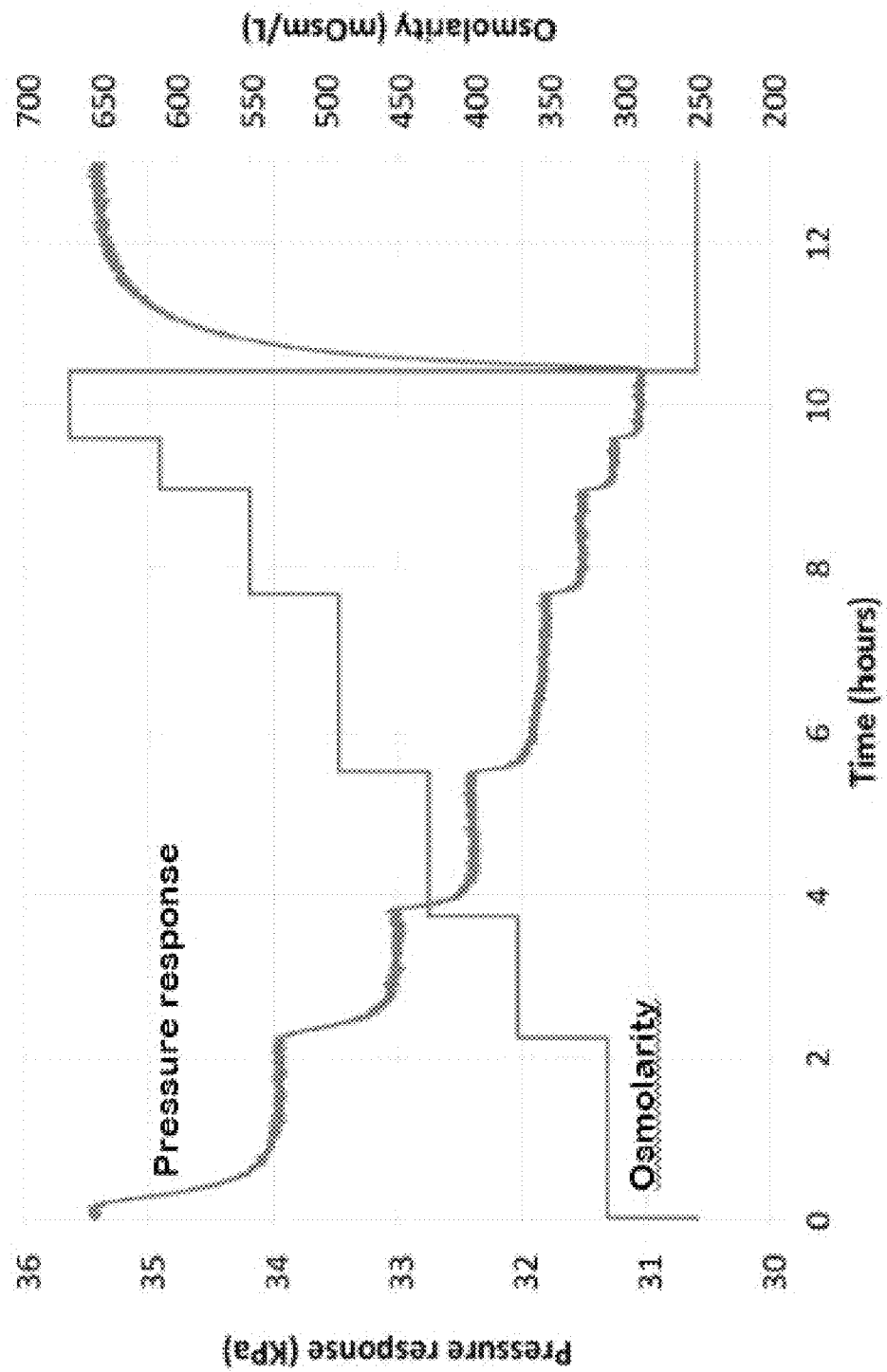
FIG. 5 is a plot of the pressure changes in the chamber over time as the concentration of the 1× phosphate-buffered saline (osmolarity) was increased stepwise for an exemplary hydrogel (hydrogel containing residues of (3-acrylamidopropyl)trimethylammonium chloride (ATMA), a quaternary amine, at 9 mole %) used in the sensors of the invention.
Figure 6:
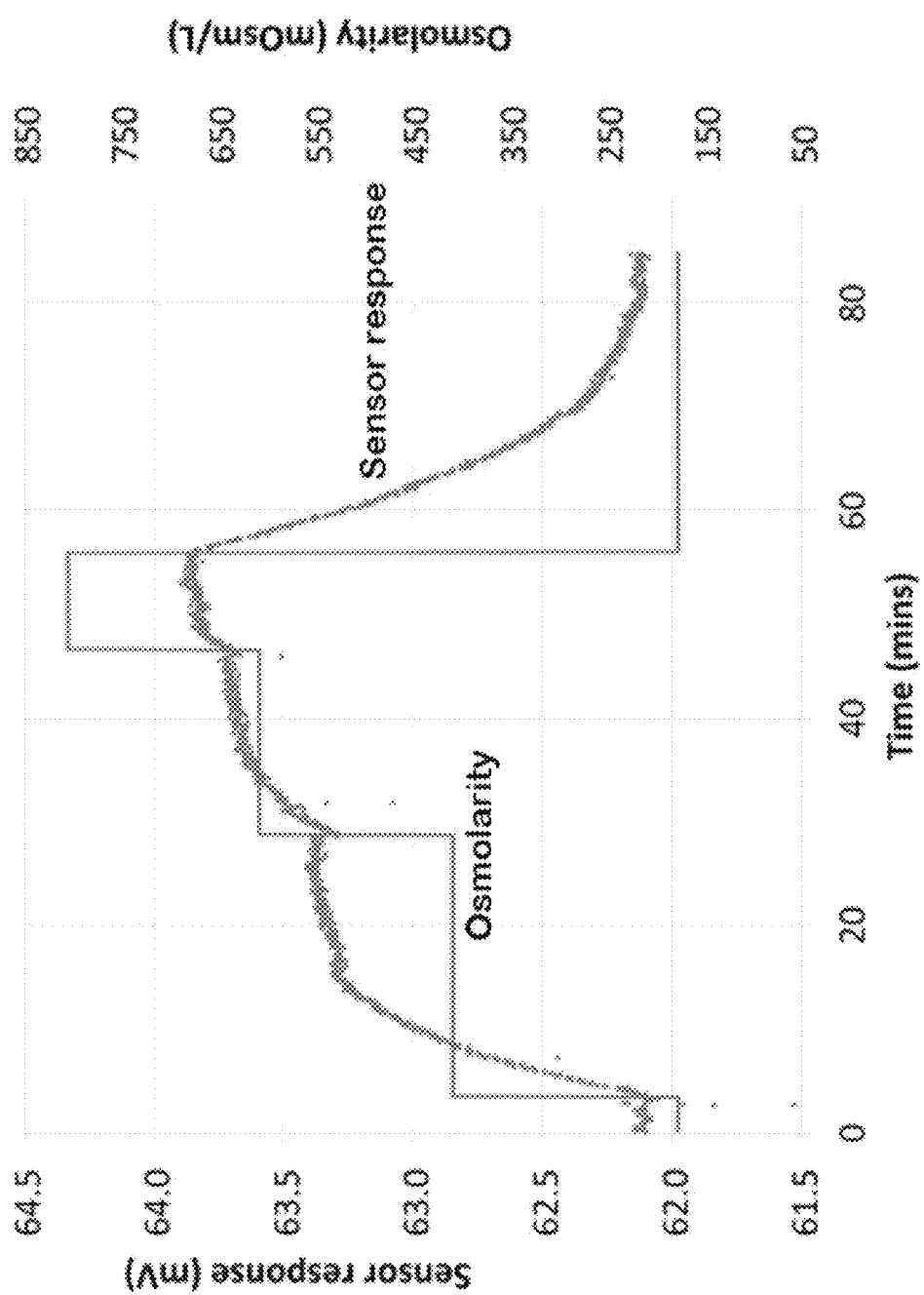
FIG. 6 is a plot of the pressure changes in the chamber over time as the concentration of the cell culture media (CDM4CHO; Dynamis) (osmolarity) was increased stepwise for an exemplary (hydrogel containing residues of (3-acrylamidopropyl)trimethylammonium chloride (ATMA), a quaternary amine, at 9 mole %) used in the sensors of the invention.

Hydrogel 1 showed good response to osmolarity and also had appropriate mechanical strength for developing sensors. Sensitivity of Hydrogel 1 was tested in 1× PBS and CDM4CHO media. As FIG. 5 and FIG. 6 show, Hydrogel 1 was able to response with osmolarity from 250 to 670 mOSm/L.

When ranges are used herein for physical properties, such as molecular weight, or chemical properties, such as chemical formulae, all combinations, and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:
1. A sensor, comprising:
   a hydrogel that is sensitive to changes in osmolarity and substantially insensitive to changes in pH, comprising:
      a hydrated, crosslinked copolymer comprising residues of the formula:

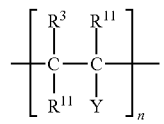

wherein:
n is at least 1,000;
Y is —(C=O)—Z or
Y is

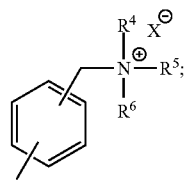

Z is —NR$^1$R$^2$ or —OR$^7$;
each of R$^1$ and R$^2$ is independently H, (C$_1$-C$_6$)alkyl, benzyl, residue derived from —(C$_1$-C$_6$)alkylenyl- NH—C=O—CH=CH$_2$ or a quaternary ammonium-substituted linker group and counteranion; and optionally, wherein at least a portion of said R$^1$ or said R$^2$ in said copolymer are said residues derived from —(C$_1$-C$_6$)alkylenyl-NH—C=O—CH=CH$_2$;

at least one of a portion of said R$^1$, said R$^2$, or said R$^7$ in said copolymer are said quaternary ammonium-substituted linker group and counteranion;

each R$^3$ is independently H or (C$_1$-C$_6$)alkyl;

each R$^4$, R$^5$, and R$^6$ is independently (C$_1$-C$_6$)alkyl;

each R$^7$ is independently (C$_1$-C$_6$)alkyl, benzyl, or said quaternary ammonium-substituted linker group and counteranion; and each R$^{11}$ is independently H or (C$_1$-C$_4$)alkyl; and a transducer associated with said hydrogel to convert a change in a physical quantity or a chemical quantity associated with said hydrogel to an electrical signal.

2. The sensor of claim 1, wherein said copolymer further comprises:
at least one residue of:
hydroxy(C$_1$-C$_6$)alkyl(meth)acrylate;
(meth)acrylic acid;
alkyl ethers;
vinyl ether;
vinyl pyrrolidone;
styrene copolymerized with allyl alcohol;
4-vinylphenol;
vinyl acetate;
ethylene copolymerized with vinyl acetate;
a zwitterionic monomer; or
a fully-neutralized sodium acrylate monomer.

3. The sensor of claim 1, wherein said —(C$_1$-C$_6$)alkylenyl-NH—C=O—CH=CH$_2$ is -methylenyl-NH—C=O—CH=CH$_2$.

4. The sensor of claim 1, wherein said quaternary ammonium-substituted linker group is a quaternary ammonium-substituted (C$_1$-C$_6$) alkyl.

5. The sensor of claim 4, wherein said quaternary ammonium-substituted C$_1$-C$_6$ alkyl is trimethyl ammonium n-propylenyl.

6. The sensor of claim 1, wherein Y is —C$_6$H$_4$CH$_2$N$^+$(CH$_3$)$_3$Cl$^-$.

7. The sensor of claim 1, wherein said copolymer is formed from a reaction of an acrylamide, a quaternary ammonium-functionalized monomer, and optionally N,N-methylene-bisacrylamide;
wherein said quaternary ammonium-substituted linker group is 3-acrylaminopropyl)trimethylammonium chloride, quaternary ammonium-substituted (meth)acrylate, or (ar-vinylbenzyl)trimethyl ammonium chloride.

8. The sensor of claim 1, wherein said copolymer comprises the reaction product of:
75 mole % to 95 mole % of acrylamide;
6 mole % to 15 mole % of 3-acrylaminopropyl)trimethylammonium chloride or (ar-vinylbenzyl)trimethyl ammonium chloride; and
0.5 mole % to 10 mole % of N,N-methylene-bisacrylamide.

9. The sensor of claim 1, wherein said copolymer comprises the reaction product of:
78 mole % to 92 mole % of acrylamide;
7 mole % to 12 mole % of 3-acrylaminopropyl)trimethylammonium chloride or (ar-vinylbenzyl)trimethyl ammonium chloride; and
1 mole % to 5 mole % of N,N-methylene-bisacrylamide.

10. The sensor of claim 1, wherein said copolymer comprises the reaction product of:
87 mole % to 89 mole % of acrylamide;
9 mole % to 11 mole % of 3-acrylaminopropyl)trimethylammonium chloride or (ar-vinylbenzyl)trimethyl ammonium chloride; and
2 mole % to 4 mole % of N,N-methylene-bisacrylamide.

11. The sensor of claim 1, wherein said counteranion is an anion selected from the group consisting of a halide and methyl sulfate.

12. The sensor of claim 1, wherein said counteranion is a fluoride ion, a chloride ion, or an iodide ion.

13. The sensor of claim 1, further comprising:
a plurality of magnetic particles associated with said hydrogel.

14. The sensor of claim 1, wherein said hydrogel is contained in a chamber of a fixed volume.

15. The sensor of claim 1, wherein said transducer is a pressure transducer, a magnetic sensor, an optical sensor, an electrical sensor, or a viscoelastic sensor.

16. The sensor of claim 1, wherein said sensor is a single-use sensor.

17. The sensor of claim 1, further comprising:
a signal transmitter for transmitting said electrical signal to a controller.

18. The sensor of claim 17, wherein said signal transmitter is reusable.

19. The sensor of claim 17, wherein said signal transmitter is wireless.

20. A sensor system, comprising:
an array of sensors, the array of sensors comprising the sensor of claim 1; and
a signal transmitter for transmitting said electrical signal to a controller.

21. The sensor system of claim 20, wherein said array of sensors is prepared by inkjet printing.

22. A method of measuring osmolarity of a fluid, comprising:
contacting the sensor of claim 1 with said fluid;
measuring a value of a physical change in said hydrogel; and
converting said value to an electrical signal;
wherein said physical change is a change in volume, a change in magnetic field, or a change in an optical property.

* * * * *